US010996225B2

(12) United States Patent
Jeahrling et al.

(10) Patent No.: US 10,996,225 B2
(45) Date of Patent: May 4, 2021

(54) METHOD FOR DETECTING PROTEIN MODIFICATIONS USING SPECIFIC ANTIBODIES

(71) Applicant: MERCK PATENT GMBH, Darmstadt (DE)

(72) Inventors: Frank Jeahrling, Muehltal (DE); Friedhelm Bladt, Heidelberg (DE); Jessica Witzgall, Dieburg (DE)

(73) Assignee: MERCK PATENT GMBH, Darmstadt (DE)

( * ) Notice: Subject to any disclaimer, the term of this patent is extended or adjusted under 35 U.S.C. 154(b) by 322 days.

(21) Appl. No.: 15/301,036

(22) PCT Filed: Feb. 27, 2015

(86) PCT No.: PCT/EP2015/000469
§ 371 (c)(1),
(2) Date: Sep. 30, 2016

(87) PCT Pub. No.: WO2015/149903
PCT Pub. Date: Oct. 8, 2015

(65) Prior Publication Data
US 2017/0023581 A1    Jan. 26, 2017

(30) Foreign Application Priority Data

Mar. 31, 2014   (EP) .................................. 14001200

(51) Int. Cl.
| | | |
|---|---|---|
| G01N 31/00 | (2006.01) | |
| G01N 33/53 | (2006.01) | |
| G01N 33/68 | (2006.01) | |
| G01N 33/573 | (2006.01) | |
| G01N 33/58 | (2006.01) | |
| G01N 33/574 | (2006.01) | |

(52) U.S. Cl.
CPC .. *G01N 33/6803* (2013.01); *C12Y 207/10001* (2013.01); *C12Y 304/11018* (2013.01); *G01N 33/573* (2013.01); *G01N 33/574* (2013.01); *G01N 33/582* (2013.01); *G01N 33/6839* (2013.01); *G01N 2333/912* (2013.01); *G01N 2333/948* (2013.01); *G01N 2440/14* (2013.01)

(58) Field of Classification Search
None
See application file for complete search history.

(56) References Cited

U.S. PATENT DOCUMENTS

| | | | |
|---|---|---|---|
| 5,891,650 | A | 4/1999 | Godowski et al. |
| 5,914,237 | A | 6/1999 | Godowski et al. |
| 6,025,145 | A | 2/2000 | Godowski et al. |
| 7,691,635 | B2 | 4/2010 | Laayoun et al. |
| 7,888,050 | B2 * | 2/2011 | Reagan ................. C07K 16/18 435/7.1 |
| 7,981,633 | B2 | 7/2011 | Henzler et al. |
| 2013/0052669 | A1 | 2/2013 | Paulovich et al. |

FOREIGN PATENT DOCUMENTS

| | | |
|---|---|---|
| JP | 2007530024 T2 | 11/2007 |
| JP | 2009501516 T2 | 1/2009 |
| WO | 9514930 A1 | 6/1995 |
| WO | 07009613 A1 | 1/2007 |

OTHER PUBLICATIONS

Du et al. Nat. Biotechnol. Jan. 2009, vol. 27., No. 1, pp. 77-83.*
Du et al. Nat. Biotechnology, Jan. 2009, vol. 27, No. 1, pp. 77-83.*
Tascilar et al. (Annals of Oncology 10,Suppl. 4:S107-S110, 1999).*
Tockman et al. (Cancer Research 52:2711s-2718s, 1992).*
Poetz et al. (Molecular & Cellular Proteomics, vol. 9, pp. 2474-2481, 2010) (Year: 2010).*
Du et al. (Nat Biotechnol. vol. 27, No. 1, pp. 77-83, Jan. 2009) (Year: 2009).*
Crompton et al. (Cancer Research, vol. 73, No. 9, pp. 2873-2838, 2013, published online Mar. 27, 2013). (Year: 2013).*
International Search Report for PCT/EP2015/000469 dated May 22, 2016.
Dunbar, S. A. et al., "Introduction to Luminex xMAP Technology and Applications for Biological Analysis in China," Asiabiotec, Oct. 1, 2010.
Raybiotech, Inc., "Human RTK Phosphorylation Antibody Array G-Series 1 for Simultaneously Detecting the Relative Level of Tyrosin Phosphorylation of Human Receptor Tyrosin Kinases (RTKs)," Mar. 12, 2008.
Reaction Biology Corporation, "Kinase Profiling & Screening," Jun. 1, 2014.

(Continued)

*Primary Examiner* — Lisa V Cook
(74) *Attorney, Agent, or Firm* — Millen, White, Zelano & Branigan, PC

(57) ABSTRACT

Method, kit and composition for analyzing analytes for modifications using modification site specific antibodies to bind an analyte with his specific modification sites of interest to different dyes simultaneously with an antibody which is specific to the non-modificated analyte binding to another dye to determine the concentration of the analyte for quantification of the modified analyte in the identical sample.

14 Claims, 8 Drawing Sheets

(56) References Cited

OTHER PUBLICATIONS

Second Office Action in corresponding Japanese Patent Application No. 2016-559913 dated Aug. 27, 2019 (pp. 1-3).
Randy Johnson, et al., Cellular Analysis Using Milliplex MAP TGF-β SignalingPathway Panel, Millipore, 2012.
Randy Johnson,, et al., Abstract 1237: TGF-β signaling pathway analysis using Milliplex MAP TGF-β multiplex panel, Proceedings:AACR 103rd Annual Meeting 2012, 2012, DOI:10.1158/1538-7445.AM2012-1237 Published Apr. 2012.
Bernsteel DJ, et al., In vitro protein kinase activity measurement by flow cytometry., Anal Biochem., Dec. 8, 2008, vol. 383, No. 2, p. 180-185, doi: 10.1016/j.ab.2008.08.026. Epub Sep. 2008 (Abstract).

* cited by examiner

METHOD FOR DETECTING PROTEIN MODIFICATIONS USING SPECIFIC ANTIBODIES

FIELD OF THE INVENTION

The subject matter of the invention is an assay which combines the Sandwich-ELISA technique for the detection of a specific analyte with the Luminex-xMAP detection technology for the identification of rare amounts of analytes in different sample matrices (e.g. cell lysates, tissue homogenates, body fluid). The detection system allows the measurement of up to 500 different analytes in one cavity.

BACKGROUND OF THE INVENTION

With the availability of a burgeoning sequence database, genomic applications demand faster and more efficient methods for the global screening of protein expression in cells. However, the complexity of the cellular proteome expands substantially if protein post-translational modifications are also taken into account.

Dynamic post-translational modification of proteins is important for maintaining and regulating protein structure and function. Among the several hundred different types of post-translational modifications characterized to date, protein phosphorylation plays a prominent role. Enzyme-catalyzed phosphorylation and dephosphorylation of proteins is a key regulatory event in the living cell. Complex biological processes such as cell cycle, cell growth, cell differentiation, and metabolism are orchestrated and tightly controlled by reversible phosphorylation events that modulate protein activity, stability, interaction and localization. Perturbations in phosphorylation states of proteins, e.g. by mutations that generate constitutively active or inactive protein kinases and phosphatases, play a prominent role in oncogenesis. Comprehensive analysis and identification of phosphoproteins combined with exact localization of phosphorylation sites in those proteins ('phosphoproteomics') is a prerequisite for understanding complex biological systems and the molecular features leading to disease. Protein phosphorylation represents one of the most prevalent mechanisms for covalent modification. It is estimated that one third of all proteins present in a mammalian cell are phosphorylated and that kinases, enzymes responsible for that phosphorylation, constitute about 1-3% of the expressed genome. Organisms use reversible phosphorylation of proteins to control many cellular processes including signal transduction, gene expression, the cell cycle, cytoskeletal regulation and apoptosis. A phosphate group can modify serine, threonine, tyrosine, histidine, arginine, lysine, cysteine, glutamic acid and aspartic acid residues. However, the phosphorylation of hydroxyl groups at serine (90%), threonine (10%), or tyrosine (0.05%) residues are the most prevalent, and are involved among other processes in metabolism, cell division, cell growth, and cell differentiation. Because of the central role of phosphorylation in the regulation of life, much effort has been focused on the development of methods for characterizing protein phosphorylation. Many of these phosphorylation sites regulate critical biological processes and may prove to be important diagnostic or therapeutic targets for molecular medicine. For example, of the more than 100 dominant oncogenes identified to date, 46 are protein kinases.

Many cancers are characterized by disruptions in cellular signaling pathways that lead to uncontrolled growth and proliferation of cancerous cells. Receptor tyrosine kinases (RTKs) play a pivotal role in these signaling pathways, transmitting extracellular molecular signals into the cytoplasm and/or nucleus of a cell. Cells of virtually all tissue types express transmembrane receptor molecules with intrinsic tyrosine kinase activity through which various growth and differentiation factors mediate a range of biological effects (reviewed in Aaronson, Science 254: 1146-52 (1991).

The catalytic activity of tyrosine kinases is frequently stimulated by autophosphorylation within a region of the kinase domain termed the activation segment (Weinmaster et al. (1984) Cell 37, 559-568), and indeed this has been viewed as the principal mechanism through which RTKs are activated (Hubbard and Till (2000) Annu. Rev. Biochem. 69, 373-398 and Hubbard, (1997) EMBO J. 16, 5572-5581). Structural analysis of the isolated kinase domains of several receptors has revealed how the activation segment represses kinase activity, and the means by which phosphorylation releases this autoinhibition. In the case of the inactive insulin receptor, Tyr 1162 in the activation segment protrudes into the active site, and the activation segment blocks access to the ATP-binding site (Hubbard et al., (1994) Nature 372, 746-754). Autophosphorylation of Tyr 1162 and two adjacent tyrosine residues repositions the activation segment, thereby freeing the active site to engage exogenous substrates and reorganizing the residues required for catalysis into a functional conformation (Hubbard (1997) EMBO J. 16, 5572-5581). In contrast, the activation segment of the fibroblast growth factor (FGF) receptor is relatively mobile and the tyrosines, which become phosphorylated upon receptor activation, do not occupy the active site. However, the C-terminal end of the FGFR1 activation segment appears to block access to substrate (Mohammadi et al. (1996) Cell 86, 577-587).

Receptor tyrosine kinases within the scope of the present invention include but are not limited to epidermal growth factor receptor (EGFR), PDGF receptor, insulin receptor tyrosine kinase (IRK), Met receptor tyrosine kinase, fibroblast growth factor (FGF) receptor, insulin receptor, insulin growth factor (IGF-1) receptor, TrkA receptor, TIE-1, Tek/Tie2, Flt-1, Flk, VEGFR3, EGFR (HER-1, ERBB2 (HER-2), ERBB3 (HER-3), ERBB4 (HER-4), Ret, Kit, Alk, Axl1, FGFR1, FGFR2, FGFR3 and Eph receptors.

Biological relationships between various human malignancies and disruptions in growth factor-RTK signal pathways are known to exist. For example, overexpression of EGFR-family receptors is frequently observed in a variety of aggressive human epithelial carcinomas, such as those of the breast, bladder, lung and stomach (see, e.g., Neal et al., Lancet 1: 366-68 (1985); Sainsbury et al., Lancet 1: 1398-1402 (1987)). Similarly, overexpression of HER2 has also been correlated with other human carcinomas, including carcinoma of the stomach, endometrium, salivary gland, bladder, and lung (see, e.g. Yokota et al., Lancet 1: 765-67 (1986); Fukushigi et al., Mol. Cell. Biol. 6: 955-58 (1986)). Phosphorylation of such RTKs activates their cytoplasmic domain kinase function, which in turns activates downstream signaling molecules. RTKs are often phosphorylated at multiple different sites, such as distinct tyrosine residues. These enzymes are gaining popularity as potential drug targets for the treatment of cancer. For example, Iressa™, an inhibitor of EGFR, has recently entered clinical trials for the treatment of breast cancer. Similarly, Gleevec™, an inhibitor of BCR/ABL, is now widely used for the treatment of CML. The great advantage of targeted therapeutics, which seek to alter the activity of a single protein, over conventional chemotoxic or radiation therapies is, that they specifically target the deregulated cell and therefore, should not have the wide cytotoxicity and adverse side effects seen with current therapies. Abnormal proliferation, differentiation, and/or dysfunction of cells are considered to be the cause of many diseases. Protein kinases and related molecules play an important role in controlling these cells so that they are very important drug targets.

Protein kinases are critical components of cellular signaling cascades that control cell proliferation and other responses to external stimuli. Modulating these signaling cascades through the inhibition of kinases has the potential to impact many diseases and conditions, including cancer, inflammation, diabetes, and stroke.

Cancer is the second leading cause of death in the western world. Despite advances in diagnosis and treatment, overall survival of patients remains poor. Scientific advances in recent years have enhanced our understanding of the biology of cancer. Human protein tyrosine kinases (PTKs) play a central role in human carcinogenesis and have emerged as the promising new targets. Several approaches to inhibit tyrosine kinase have been developed. These agents have shown impressive anticancer effects in preclinical studies and are emerging as promising agents in the clinic. The remarkable success of BCR-ABL tyrosine kinase inhibitor imatinib (Gleevec™) in the treatment of chronic myeloid leukaemia has particularly stimulated intense research in this field. At least 30 inhibitors are in various stages of clinical development in cancer, and about 120 clinical trials are ongoing worldwide. Innovative approaches are needed to fully evaluate the potential of these agents, and a concerted international effort will hopefully help to integrate these inhibitors in cancer therapy in the near future.

As a result, protein kinases have become one of the most prominent target families for drug development. Hence, there is an urgent need to develop newer more effective therapies to improve patient outcomes.

Rapid scientific advances in recent years have enhanced our understanding of the biology of cancer. Consequently, several novel targets have been identified. Tyrosine kinases have emerged as a new promising target for cancer therapy. Many small molecule kinase inhibitors are currently in development, and the approvals of Gleevec™ (Novartis; leukemia, gastrointestinal tumors) and Iressa™ (AstraZeneca; lung cancer) have validated the inhibition of kinases as a highly promising therapeutic strategy.

Human genome sequence analysis has identified about 518 human protein kinases (constituting about 1.7% of all the human genes). Within this large protein kinase complement, at least 90 tyrosine kinase genes have been identified (58 receptor tyrosine kinases (RTKs, Table 1) and 32 non-receptor tyrosine kinases (NRTKs, Table 2). The cell signalling pathways they initiate are complex (Schlessinger J. et al. Cell 103 (2000), pp. 211-225). In brief, receptor tyrosine kinases (RTKs) contain an amino-terminal extracellular ligand-binding domain (usually glycosylated), a hydrophobic transmembrane helix, and a cytoplasmic domain, which contains a conserved protein tyrosine kinase core and additional regulatory sequences (that contain crucial C-terminal tyrosine residues and receptor regulatory motifs). Ligand binding (HGF, IGF, EGF, TGF-, or others) to the extracellular domain (ECD) results in receptor dimerisation/oligomerisation, leading to activation of cytoplasmic tyrosine kinase activity and phosphorylation of tyrosine residues (Schlessinger et al., Neuron (1992) 9:383-391). Autophosphorylated tyrosine residues serve as a platform for the recognition and recruitment of a specific set of signal-transducing proteins (such as proteins containing SH2 (Src homology 2) and PTB (phosphotyrosine binding) domains) that modulate diverse cell signalling responses. Nonreceptor tyrosine kinases have a common conserved catalytic domain (similar to RTKs) with a modular N-terminal, which has different adapter protein motifs. Tyrosine kinases play a critical role in the regulation of fundamental cellular processes including cell development, differentiation, proliferation, survival, growth, apoptosis, cell shape, adhesion, migration, cell cycle control, T-cell and B-cell activation, angiogenesis, responses to extracellular stimuli, neurotransmitter signalling, platelet activation, transcription, and glucose uptake (Hunter T. Philos. Trans. R. Soc. Lond., B Biol. Sci. 353 (1998), pp. 583-605). Given their pivotal role in normal homeostasis, it is perhaps not surprising that they have been implicated in several human disorders including developmental anomalies (craniosynostosis syndromes and others), immunodeficiency (severe combined immunodeficiency disease (SCID), hereditary agammaglobulinaemia), non-insulin-dependent diabetes mellitus (NIDDM), atherosclerosis, psoriasis, renal disease, neurological disorders, leukaemia, and solid tumors (Madhusudan S. and Ganesan T S. Clin Biochem. 2004 July; 37(7):618-35).

TABLE 1

Receptor tyrosine kinases and cancer

| Tyrosine kinase | Cancer associations |
| --- | --- |
| EGFR family | |
| EGFR (HER-1) | Breast, ovary, lung, glioblastoma multiforme, and others |
| ERBB2 (HER-2) | Breast, ovary, stomach, lung, Colon, and others |
| ERBB3 (HER-3) | Breast |
| ERBB4 (HER-4) | Breast, granulosa cell tumors |
| Insulin R family | |
| IGF-1R | Cervix, kidney (clear cell), sarcomas, and others |
| IRR, INSR | — |
| PDGFR family | |
| PDGFR-a | Glioma, glioblastoma, ovary |
| PDGFR-β | Chronic myelomonocytic leukaemia (CMML), glioma |
| CSF-1R | CMML, malignant histiocytosis, glioma, endometrium |
| KIT/SCFR | GIST, AML, myelodysplasia, mastocytosis, seminoma, lung |
| FLK2/FLT3 | Acute myeloid leukaemia (AML) |
| VEGFR family | |
| VEGFR1 | Tumor angiogenesis |
| VEGFR2 | Tumor angiogenesis |
| VEGFR3 | Tumor angiogenesis, Kaposi sarcoma, haemangiosarcoma |
| FGFR family | |
| FGFR-1 | AML, lymphoma, several solid tumors |
| FGFR-2 | Stomach, breast, prostate |
| FGFR-3 | Multiple myeloma |
| FGFR-4 | — |
| KLG/CCK family (CCK4) | — |
| NGFR family | |
| TRKA | Papillary thyroid cancer, neuroblastoma |

TABLE 1-continued

Receptor tyrosine kinases and cancer

| Tyrosine kinase | Cancer associations |
|---|---|
| TRKB | |
| TRKC | Congenital fibrosarcoma, acute myeloid leukaemia |
| HGFR family | |
| MET | Papillary thyroid, rhabdomyosarcoma, liver, kidney |
| RON | Colon, liver |
| EPHR family | |
| EPHA2 | Melanoma |
| EPHA1, 3, 4, 5, 6, 7, and 8 | — |
| EPHB2 | Stomach, oesophagus, colon |
| EPHB4 | Breast |
| EPHB1, 3, 5, and 6 | — |
| AXL family | |
| AXL | AML |
| MER, TYRO3 | — |
| TIE family | |
| TIE | Stomach, capillary haemagioblastoma |
| TEK | Tumor angiogenesis |
| RYK family (RYK) | Ovarian cancer |
| DDR family (DDR1 and DDR2) | Breast, ovarian cancer |
| RET family (RET) | Thyroid (papillary and medullary), multiple endocrine neoplasia |
| ROS family (ROS) | Glioblastoma, astrocytoma |
| LTK family | |
| ALK | non-Hodgkin lymphoma |
| LTK | — |
| ROR family (ROR1 and ROR2) | — |
| MUSK family (MUSK) | — |
| LMR family (AATYK, AATYK 2, and 3) | — |
| RTK106 | — |

TABLE 2

Nonreceptor tyrosine kinases and cancer

| Tyrosine kinase | Cancer associations |
|---|---|
| ABL family | |
| ABL1 | Chronic myeloid leukaemia (CML), AML, ALL, CMML |
| ARG | AML |
| FRK family | |
| BRK | Breast |
| FRK | — |
| SRMS | — |
| JAK family | |
| JAK1 | Leukaemias |
| JAK2 | AML, ALL, T-cell childhood ALL, atypical CML |
| JAK3 | Leukaemia, B-cell malignancies |
| JAK4 | — |
| SRC-A family | |
| FGR | AML, CLL, EBV-associated lymphoma |
| FYN | — |

TABLE 2-continued

Nonreceptor tyrosine kinases and cancer

| Tyrosine kinase | Cancer associations |
|---|---|
| SRC | colon, breast, pancreas, neuroblastoma |
| YES1 | colon, melanoma |
| SRC-B family | |
| BLK | — |
| HCK | — |
| LCK | T-cell ALL, CLL |
| LYN | — |
| SYK family | |
| SYK | Breast |
| ZAP70 | — |
| FAK family | |
| FAK | adhesion, invasion and metastasis of several tumors |
| PYK2 | adhesion, invasion and metastasis of several tumors |
| ACK family | |
| ACK1 | — |
| TNK1 | — |
| CSK family | |
| CSK | — |
| MATK | — |
| FES family | |
| FER | — |
| FES | — |
| TEC family | |
| BMX | — |
| BTK | — |
| ITK | — |
| TEC | — |
| TXK | — |

Tyrosine kinases play a central role in oncogenic transformation of cells. This is achieved in several ways (Blume-Jensen P. et al. Nature 411 (2001), pp. 355-365). Gene amplification and/or overexpression of PTKs (e.g., EGFR and HER-2 overexpression that is commonly seen in several cancers) cause enhanced tyrosine kinase activity with quantitatively and qualitatively altered downstream signalling. Genomic rearrangements (like chromosomal translocation) can result in fusion proteins with constitutively active kinase activity (e.g., p210BCR-ABL fusion protein seen in chronic myeloid leukaemia). Gain of function (GOF) mutations or deletion in PTKs within the kinase domain or extracellular domain result in constitutively active tyrosine kinase (e.g., EGFRvIII mutant that lacks amino acids 6-273 of the extracellular domain is constitutively active and is seen in solid tumors). Autocrine-paracrine stimulation by overexpression of ligands results in persistent tyrosine kinase stimulation (e.g., TGF- is overexpressed in glioblastoma and head and neck cancer (Grandis J. R. et al. J. Cell. Biochem. 69 (1998), pp. 55-62). Finally, retroviral transduction of a protooncogene corresponding to a PTK concomitant with deregulating structural changes is a frequent mechanism by which oncogenic transformation occurs in animals (rodents and chicken) (Blume-Jensen P. et al. Nature 411 (2001), pp. 355-365).

A significant number of tyrosine kinases (both receptor and nonreceptor types) are associated with cancers. Clinical studies suggest that overexpression/deregulation of tyrosine kinases may be of prognostic/predictive value in patients (i.e., may indicate an aggressive tumor biology or may predict poor response to therapy and shorter survival). EGFR family of tyrosine kinases is the most widely investigated. EGFR (HER-1) overexpression is associated with a poor prognosis in ovarian, head and neck, oesophageal, cervical, bladder, breast, colorectal, gastric, and endometrial cancer (Nicholson R. I et al. Eur. J. Cancer 37 Suppl. 4 (2001), pp. S9-S15). HER-2 overexpression is associated with poorer outcome in patients with breast (Tandon A. K. et al. A. K. Clin. Oncol. 7 (1989), pp. 1120-1128), ovary Meden H. et al. Eur. J. Obstet. Gynecol. Reprod. Biol. 71 (1997), pp. 173-179), prostate (Sadasivan R. et al. J. Urol. 150 (1993), pp. 126-131), lung (Selvaggi G. et al. Cancer 94 (2002), pp. 2669-2674) and bone cancer (Zhou H. et al. J. Pediatr. Hematol. Oncol. 25 (2003), pp. 27-32). Mutation in C-KIT tyrosine kinase is associated with inferior survival in patients with gastrointestinal stromal tumors (Taniguchi M. et al. Cancer Res. 59 (1999), pp. 4297-43) and adversely affects relapse rate in acute myeloid leukaemia (Care R. S. et al. Br. J. Haematol. 121 (2003), pp. 775-777). In small cell lung cancer, C-KIT expression was linked to poor survival (Naeem M. et al. Hum. Pathol. 33 (2002), pp. 1182-1187). The expression of IGF-1R along with IGF-1 and IGF-2 may have prognostic value in a subset of colorectal cancer patients (Peters G. et al. Virchows Arch. (2003). In acute myeloid leukaemia, FLT 3 mutation predicts higher relapse rate and a shorter event free survival (Schnittger S. et al. Blood 100 (2002), pp. 59-66). VEGF is a central growth factor that drives tumor angiogenesis and is an important prognostic marker in solid tumors (Fox S. B. et al. Lancet Oncol. 2 (2001), pp. 278-289). Recent studies suggest that VEGFR 3 expression in lung cancer is associated with a significantly lower survival rate (Arinaga M. et al. Cancer 97 (2003), pp. 457-464) and in colorectal cancer, it may have prognostic significance (Parr C. et al. Int. J. Oncol. 23 (2003), pp. 533-539). Trk tyrosine kinase is an important marker for neuroblastoma (NB). TrkA is present in NB with favourable biological features and highly correlated with patient survival, whereas TrkB is mainly expressed on unfavourable, aggressive NB with MYCN-amplification (Eggert A. et al. Klin. Padiatr. 212 (2000), pp. 200-205). HGFR (Met) overexpression is associated with disease progression, recurrence, and inferior survival in early-stage invasive cervical cancer (Baycal C. et al. Gynecol. Oncol. 88 (2003), pp. 123-129) correlates with poor prognosis in synovial sarcoma (Oda Y. et al. Hum. Pathol. 31 (2000), pp. 185-192) and predicts a significantly shorter 5-year survival in hepatocellular carcinoma (Ueki T. et al. Hepatology 25 (1997), pp. 862-866). Axl tyrosine kinase expression was associated with poor outcome in acute myeloid leukaemia (Rochlitz C. et al. Leukemia 13 (1999), pp. 1352-1358). Tie-1 kinase expression inversely correlates with survival in gastric cancer (Lin W. C. et al. Clin. Cancer Res. 5 (1999), pp. 1745-1751) and in early chronic phase chronic myeloid leukaemia (Verstovsek S. et al. Cancer 94 (2002), pp. 1517-1521). Soluble Tie-2 receptor levels independently predict loco-regional recurrence in head and neck squamous cell (Homer J. J. et al. Head Neck 24 (2002), pp. 773-778). ALK protein expression is an independent predictor of survival and serves as a useful biologic marker of a specific disease entity within the spectrum of anaplastic large cell lymphoma (ALCL, Gascoyne R. D. et al. Blood 93 (1999), pp. 3913-3921). Src tyrosine kinase is an independent indicator of poor clinical prognosis in all stages of human colon carcinoma (Aligayer H. et al. Cancer 94 (2002), pp. 344-351). BCR-ABL tyrosine kinase is of prognostic value and predicts response to therapy in haematological malignancies including chronic myeloid leukaemia (Olavarria E. et al. Blood 97 (2001), pp. 1560-1565 and O'Dwyer M., et al. Oncologist 7 Suppl. 1 (2002), pp. 30-38) and acute lymphoblastic leukaemia (Gleissner B. et al. Blood 99 (2002), pp. 1536-1543) FAK overexpression is correlated with tumor invasiveness and lymph node metastasis in oesophageal squamous cell carcinoma (Miyazaki, T. et al. Br. J. Cancer 89 (2003), pp. 140-145) and reduced expression of the Syk gene is correlated with poor prognosis in breast cancer (Toyama T. et al. Cancer Lett. 189 (2003), pp. 97-102).

Several approaches to target tyrosine kinases have been developed. Tyrosine kinase domain inhibitors, tyrosine kinase receptor blockers (e.g., monoclonal antibodies), ligand modulators (e.g., monoclonal antibodies), RNA interference and antisense technology, gene therapy strategy, inhibitors of Src tyrosine kinase, BCR-ABL inhibitors, downstream signal transduction pathway inhibitor are potential strategies for cancer therapy. Classification of such inhibitors based on their mode of action is summarized in Table 3. Receptor tyrosine kinases are multidomain proteins. The catalytic domain (Mg-ATP complex binding site) has emerged as the most promising target for drug design in recent years. Random screening of compound libraries initially identified small molecule chemical inhibitors of the catalytic domain. Combinatorial chemistry, in-silico cloning, structure-based drug design, and computational chemistry have now become indispensable tools in lead compound identification and optimisation of these inhibitors. Highly sensitive, accurate, and reliable high throughput assays for screening inhibitors have been developed (including scintillation proximity assay, fluorescence polarisation assay, homogenous time-resolved fluorescence assay, and the heterogeneous time-resolved dissociation-enhanced fluorescence technology (F. A. Al-Obeidi and K. S. Lam, Oncogene 19 (2000), pp. 5690-5701). Knowledge about tertiary structure of protein kinases has expanded, and the X-ray crystallographic structure for over 50 protein kinases has been resolved. Understanding of the molecular interactions of the various parts of the 'ATP-binding site' (adenine region, sugar region, hydrophobic pocket, hydrophobic channel, and the phosphate-binding region) has accelerated drug development (Fabbro D. et al. Pharmacol. Ther. 93 (2002), pp. 79-98).

TABLE 3

Classification of inhibitors

| Small molecule inhibitors | Ligand modulation |
| --- | --- |
| Targeting EGFR | Targeting VEGF |
| ZD1839 (Iressa, Gefitinib) | Bevacizumanb (RhuMAb, Avastink) |
| OSI-774 (Tarceva, Erlotinib, CP-358774) | MV833 |
| | Soluble Flt-1 and Flk-1 |
| PKI-166 | VEGF Trap |
| CI-1033 (PD183805) | GFB 116 |
| CGP-59326A | NM3 |
| EKB-569 | VEGF 121-diphtheria toxin conjugate |
| GW 572016 | |
| Targeting HER-2/neu | Targeting EGF |
| PKI-166 (also inhibits EGFR) | DAB389EGF (diphtheria toxin conjugate) |
| TAK165 | Targeting FGF |
| GE-572016 (inhibits EGFR) | Interferon-a (reduces FGF production) |
| CI-1033 (pan erbB inhibitor) | |
| Targeting VEGFR | Monoclonal antibodies against receptors |
| SU5416 (also targets FLT3) | |
| ZD4190 | Targeting EGFR |
| PTK787/ZK222584 | IMC-C225 (Cetuximab) |

TABLE 3-continued

Classification of inhibitors

| Small molecule inhibitors | Ligand modulation |
|---|---|
| CGP 41251 | ABX-EGF |
| CEP-5214 | Y10 |
| ZD6474 (also inhibits RET) | MDX-447 (EMD 82633) |
| BIBF1000 | h-R3 |
| VGA1102 | EMD 72000 |
| SU6668 (also inhibits PDGFR and FGFR) | Targeting HER-2/neu |
| | Herceptin (trastuzumab) |
| Targeting PDGFR | MDX-H210 |
| SU11248 (also inhibits C-KIT, FLT-3) | 2C4 (pertuzumab) |
| | Targeting VEGFR |
| CGP-57148 | IMC-1C11 (anti-KDR antibody) |
| Tricyclic quinoxalines (also targets C-KIT) | Anti-Flt-1 antibody (MF1) |
| Targeting FGFR | Gene therapy approaches |
| SU4984 | Targeting EGFR |
| SU5406 | Antisense oligonucleotide |
| Targeting BCR-ABL | Targeting VEGF/VEGFR |
| STI571 (Glivec) (also targets C-KIT, PDGFR) | Antisense oligonucleotides |
| | Adenovirus-based Flt-1 gene therapy |
| NSC680410 | Retrovirus-based Flk-1 gene therapy |
| Targeting C-KIT | Retrovirus-based VHL gene therapy |
| PD166326 (also targets BCR-ABL) | Angiozyme |
| | Targeting IGF-1R |
| PD1173952 (also targets BCR-ABL) | INX-4437 (Antisense oligonucleotides) |
| Targeting FLT3 | Others |
| CT53518 | APC8024 (vaccine against HER-2 overxpressing cells) |
| GTP14564 | |
| PKC412 | AP22408 (Src SH2 domain inhibitor) |
| Targeting Src | B43-genistein conjugate |
| PP1 (also inhibits C-KIT, BCR-ABL) | AG538 (IGF-1R inhibitor) |
| PD116285 | |
| CGP77675 | |
| CGP 76030 | |
| Targeting TRK | |
| CEP-701 (also inhibits Flt 3) | |
| CEP2583 | |

Although ATP-binding site is highly conserved among tyrosine kinases, minor differences in kinase domain architecture have allowed development of highly selective inhibitors (Levitzki A. Eur. J. Cancer 38 Suppl. 5 (2002), pp. S11-S18). Data on EGFR co crystallised with its inhibitor OSI-774 (Tarceva™) were published recently and provide valuable insight into the mechanism of action of this compound (Stamos J. at al. J. Biol. Chem. 277 (2002), pp. 46265-46272). Most small molecules in clinical development bind in the vicinity of the ATP-binding site of their target kinases, using a part of their scaffold to mimic the binding of the adenine moiety of ATP. Such ATP mimics are competitive inhibitors of the substrate-binding sites within the catalytic domain (Laird A. D. et al. Expert Opin. Invest. Drugs 12 (2003), pp. 51-64 and Fry D. W. Exp. Cell Res. 284 (2003), pp. 131-139) and compete with endogenous ATP (often present in millimolar levels in cells) for binding. Early potent lead compounds had poor solubility and required extended multiple dosing schedules to achieve and maintain adequate plasma levels in patients necessary for optimal target inhibition. To increase solubility, new compounds were generated, but they had reduced affinity to the kinase domain. To circumvent these problems, irreversible inhibitors are now being developed in the hope that covalent attachment of a selective inhibitor to the kinase domain would completely abolish catalytic activity and would translate into potent drugs (Denny W. A. et al. Pharmacol. Ther. 93 (2002), pp. 253-261). Two such inhibitors are in advanced stage of development (CI-1033) (Pfizer) and EKB-569 (Wyeth) that bind irreversibly to EGFR and HER-2, respectively (Laird A. D. et al. Expert Opin. Invest. Drugs 12 (2003), pp. 51-64). Small molecules that target more than one tyrosine kinase have also been developed, and they have the potential to block multiple pathways and produce enhanced anticancer effect (Table 3). PKI-166 inhibits EGFR and HER-2 (Mellinghoff I. K. et al. Cancer Res. 62 (2002), pp. 5254-5259CI-1033) is a pan ErbB inhibitor (Slichenmyer, W. J. et al. Semin. Oncol. 28 (2001), pp. 80-85), SU6668 inhibits VEGFR, PDGFR, and FGFR (Hoekman K. et al. 7 Cancer J. Suppl. 3 (2001), pp. S134-S13, and STI 571 inhibits BCR-ABL, C-KIT, PDGFR, and ARG (Buchdunger, E. et al. Eur. J. Cancer 38 Suppl. 5 (2002), pp. S28-S36. and Nishimura N. et al. Oncogene 22 (2003), pp. 4074-4082.

In the 1980s, first natural tyrosine kinase inhibitors quercetin and genistein were reported (Akiyama T. et al. J. Biol. Chem. 262 (1987), pp. 5592-5595 and J. Mendelsohn J. J. Clin. Oncol. 20 (2002), pp. 1S-13S).

Since then, an overwhelming number of natural and synthetic small molecules inhibitors have been described. Tyrosine kinase inhibitors can be broadly categorised into natural products and related derivatives (quercetin, genistein, staurosporine, erbastatins, clavilactones); quinazolines, pyridopyrimidines, and related heterocycles (e.g., ZD1839); phenylamino-pyrimidines (e.g., STI 571); tryphostins and analogues (e.g., SU1498, SU101, SU0020); indoles and oxindoles (e.g., SU5416, SU6668, SU5402; F. A. Al-Obeidi and K. S. Lam, Oncogene 19 (2000), pp. 5690-5701).

One of the major difficulties in the development of small molecule kinase inhibitors is specificity (McMahon et al. (1998) Curr. Op. in Drug Discovery and Dev. 1(2), 131-146). Most compounds currently target the highly conserved ATP binding site of kinases, and therefore tend to bind and inhibit more than one enzyme in the class. Because there are more than 500 human protein kinases (Manning et al., Science (2002) 298, 1912) and inhibition of multiple kinases (or the "wrong" kinase) may lead to adverse effects, it is critical to assess compound specificity. However, the problem has been that most "off-target" interactions are not predictable and the development of conventional experimental activity assays for kinases is very time consuming and resource intensive. As a result, even though compound specificity is critically important to assess, it has been extremely difficult, if not impossible, to do so comprehensively and systematically. Protein kinases are key regulators of most cellular signaling pathways in eukaryotic cells. Many protein kinase inhibitors have been developed to study specific functions of kinases in signaling pathways and as potential therapeutic agents (Cohen, P. (2002) Nat. Rev. Drug Discov. 1, 309-315) Because of the large size of the protein kinase superfamily (>500 human) and the fact that most kinase inhibitors bind in the highly conserved ATP-binding pocket, it is widely accepted that kinase inhibitors inhibit more than one target (Davies, S. P., Reddy, H., Caivano, M. & Cohen, P. (2000) Biochem. J. 351, 95-105). As a result, the inhibitors used as chemical tools to probe the often poorly understood roles of kinases in signaling pathways are paradoxically of incompletely characterized specificity. The same is true for kinase activators. The present invention is also usable for the parallel profiling of kinase activators of multiple kinases in one cavity.

Preferred Embodiments of the Invention

The difficulties noted above are solved by an assays format that allows testing many compounds against a very large panel of human kinases (up to 500 in one cavity). A cavity can be a microtiter plate, a vial, a petri dish or another container where the assay described in the method can be performed. The assay makes it possible to assess specificity efficiently, quantitatively, comprehensively, and systematically. It is no longer necessary to grossly estimate compound specificity based on tests against only a small number of kinases. Specificity profiling can be incorporated earlier in the drug development process and along the entire development path, and specificity can be assessed systematically and rapidly for many more compounds. This unprecedented ability allows for tight feedback between medicinal chemistry and molecule testing. Potency and specificity can be optimized in parallel, leading to higher quality preclinical candidates in far less time.

Evaluating specificity comprehensively for existing late-stage candidates or drugs may also reveal previously unknown targets for these proven compounds. In some cases, the identification of new targets can suggest new indications, and in other cases may reveal the causes of side-effects that are not explained by the known, primary targets.

The subject matter of the invention is a novel approach to specificity profiling addresses one of the major bottlenecks in the development of small molecule kinase inhibitors or activators, and promises to have a major impact on the development of this important class of new drugs. The subject matter of the invention is an assay that combines the Sandwich-ELISA (enzyme-linked immunosorbent assay) technique for the detection of autophosphorylation of tyrosine kinases with the Luminex™-xMAP detection system for the identification of particular proteins in a tissue sample. A tissue sample means but is not limited to cell lysates, biopsy homogenates, tumor biopsy homogenates, diseases tissue homogenates, lysates of blood cells.

The Luminex-xMAP technology is a proven multiplex platform that uses precise ratios of three fluorescent dyes to create 500 different bead or microsphere sets that caries each another dye characterized by the unique internal fluorescent dye ratio. This dye ratio is used as an identification code for each microsphere set. By this reason each microsphere set could be measured individually and can therefore used to identify simultaneous an unique analyte. This means that in the ideal case 500 analytes could be measured by the same time in on cavity or sample.

The bead or microshere is used as a solid phase which could bind a unique capture molecule on its surface (e.g. antibodies, peptides, receptor protein) specific for the analyte. After the binding of the analyte to the specific capture molecule a second analyte specific molecule which targets another binding site of the analyte is used for the detection. This second molecule could be directly conjugated to the read out label or coupled to Biotin which is further detected by a highly specific Streptavidin conjugated read out label. A fourth fluorescent dye (Phycoerythrin) is generally used as read out label which could be distinguished from the internal dye for microsphere identification.

The assay allows detecting the presence or absence of autophosphorylation of RTKs or NTKs in presence of a potential kinase inhibitor for up to 500 different phosphorylation sites in different kinases including the total amount of the non phosphorylated kinase from e.g. a cell lysate in one cavity. The assay format allows the profiling of a potential kinase inhibitor for up to 500 different phosphorylation sites in different tyrosine kinases, by detecting the phosphorylation status within one cavity. For example the assay allows performing a profiling in a Sandwich-ELISA in a 96 well plate for 96 different potential kinase inhibitors from an HTS against a combination of up to 500 different phosphorylation sites in different kinases per well. For example up to 8 different phosphorylation sites could be measured in one kinase simultaneously.

An assay for measuring activation (i.e., autophosphorylation) of a tyrosine kinase receptor of interest is described in EP0730740 and comprises the following steps:

a) A first solid phase is coated with a substantially homogeneous population of cells from cell culture or animal material so that the cells adhere to the first solid phase. The cells have either an endogenous tyrosine kinase or have been transformed with DNA encoding a tyrosine kinase and the DNA has been expressed so that the tyrosine kinase construct is presented in the cell membranes or in the cytosol of the cells. b) A ligand is then added to the solid phase having the adhering cells, such that the tyrosine kinase is exposed to the ligand. c) Following exposure to the ligand, the adherent cells are solubilized, thereby releasing cell lysate. d) A second solid phase is coated with a capture agent as a specific antibody, which binds specifically to the tyrosine kinase, or, in the case of a receptor construct, to a polypeptide epitope tag. e) The cell lysate obtained in step c) is added to the wells containing the adhering capture agent so as to capture the tyrosine kinase to the wells. f) A washing step is then carried out, so as to remove unbound cell lysate, leaving the captured tyrosine kinase. g) The captured tyrosine kinase construct is exposed to a labeled anti-phosphotyrosine antibody which identifies phosphorylated residues in the tyrosine kinase. h) Binding of the anti-phosphotyrosine antibody to the captured tyrosine kinase is measured.

The capture agent used in the present invention that allows the parallel detection of the autophosphorylation status of up to 500 tyrosine kinases in one well was derived from the Luminex™-xMap technology. The capture agent can be a binding protein coated bead or microsphere. The binding protein will most typically be a biomolecule such as a protein or a polynucleotide. The biomolecule may optionally be a naturally occurring, recombinant, or synthetic biomolecule. Antibodies or antibody fragments are highly suitable as protein-capture agents. The binding protein can also be an aptamer or antikalin or any other binding molecule. The Luminex™-xMap technology is a proven multiplex platform that uses precise ratios of two fluorescent dyes to create 100 different bead or microsphere sets that caries each another dye characterized by the ratios of two fluorescent dyes. Each set is distinguished based on his internal fluorescent dye ratio of two different dyes and can therefore bind an unique biological reagent as a specific antibody or monoclonal antibody against a particular tyrosine kinase. Antibodies bound to bead or microsphere surfaces serve as capture reagent in the sandwich ELISA test mentioned previously. The different antibodies specific for different kinases bound to a bead surface with different fluorescent dyes ratio resulting in a different color for each specific antibody-microsphere complex. The fluorescence color can be allocated to particular kinase that serves as antigen for the specific antibody that recognizes and binds a particular epitope of a definite kinase.

A phospho-specific antibody that recognizes phosphorylated tyrosine in general was used for the measurement of the autophoshorylation of the tyrosine kinases. The phospho-specific antibody is biotinylated and can be detected by a streptavidin coupled second fluorescence label (e.g. Phycoerythrin) that can be distinguished from the fluorescent dyes of the microspheres.

Modification site and non-modification site specific antibodies are widely commercially available (e.g. from Cell Signaling Technology, Epitomics, R&D Systems; BioSource, Inc.; Santa Cruz; Biotechnology, Inc.; Merck Millipore), and may also be produced by techniques well known in the art. Monoclonal antibodies from rabbit and mouse should be preferred as capture antibodies because of their unique target specificity.

So far, the only available assay formats (designated as 'standard assay format') for the detection of a modified analyte (e.g. phosphorylated, methylated) in unprocessed samples uses the capture with an antibody specific to the total analyte on the microsphere (which bind equally to the non-modified and modified analyte) and the detection by an antibody specific for the modification site of interest or a non target specific pan-phosphotyrosine detection antibody. The detection threshold in this assay format is a combination of the total concentration of the analyte in the sample and the ratio between the non-modified and modified analyte. Because of the low abundance of modified analytes in most samples the majority of bound analyte is in the non-modified state. By this reason the small amount of the captured modified analyte could not be measured. Due to the fact that the capture molecule is identical for both, the modified or the non-modified analyte, the measurement of the different analyte forms must be performed in two independent cavities or assays. So no simultaneous measurement in one sample is possible and the results could be affected by the two different assay setups (dilutions, handling). The preferred inverse assay format uses a modification site specific antibody to bind only an analyte with his specific modification site of interest to the microsphere. The same analyte with another modification site or the non-modified analyte are not captured on this bead set. To detect the captured analyte on the microsphere an antibody which bind to a non-modification site specific region on the analyte is used which could be directly conjugated to the read out label or coupled to Biotin. As in the previous described standard assay format the Biotin is further detected by a Streptavidin conjugated read out label. This fourth fluorescent dye (Phycoerythrin) is generally used as read out label is distinguishable from the internal dye for microsphere identification. Due to the specific capturing with a modification site specific molecule a combination with a second microshere with another identification code is possible that bind the identical but non-modified analyte. By the reason of this inverse assay format non-modified and modified analytes could be measured simultaneously in one cavity without the need of processing the sample. Furthermore other modification sites on this same analyte could be comparably measured on a third, fourth or more microsphere set and can be distinguished from each other in the identical sample. This allows in future a more complex analysis of an individual analyte concerning is activation state which is strictly dependent of its different modification sites. In addition to the unique multiplexing possibility the sensitivity of the new inverse assay format for the modified analytes is dramatically increased in direct comparison with the traditional standard assay format. This improved detection threshold will allow the future measurement of very small sample sizes like needle biopsies that are currently not possible in the standard assay format of the prior art described in EP0730740 and U.S. Pat. No. 7,981,699B1 (designated as 'standard assay format').

The autophosphorylation of each captured kinase is analyzed by an instrument that is able to detect all unique fluorescent dyes colored microspheres and the streptavidin coupled fluorescence marker that binds the biotinylated anti phosphotyrosine antibody. These instruments are well known in the prior art. A Luminex™ instrument detects the different fluorescents reporter signals. In the Luminex™ instrument, the beads pass rapidly through two laser beams where high-speed digital signal processors distinguish between beads with two fluorescent signals (signal from microsphere and anti phosphotyrosine antibody signal) or one fluorescent signal (only signal from microsphere). In case of an autophosphorylation event, the phospho-specific antibody is able to bind the phosphorylated kinase that is captured by the specific antibody associated with a particular bead and two fluorescent signals can be detected. In case of lacking an autophosphorylation event only the microsphere signal is detectable by the laser. Within the three different available Luminex™ instruments the FlexMAP 3D in a high-performance analyzer which is build for the measurement of up to 500 different microsphere sets. This instrument is also created to measure 384 well plate in addition to standard 96 well plates. The original Luminex-200™ instruments is able to differentiate between 100 different microsphere sets whereas the MAGPIX is only suited for 50 different magnetic microsphere sets. This new bench-top analyzer is suitable for smaller assay formats for example in clinical studies.

All kinases in the test cell lysate that are inhibited by an added particular kinase inhibitor that will block autophosphorylation show only the microsphere signal and can be recognized as an tyrosine kinase that is inhibited by the kinase inhibitor tested. The kinase inhibitor tested does not inhibit kinases that show both signals (signal from microsphere and anti phosphotyrosine antibody signal). In an identical control cell lysate without kinase inhibitor, kinases that have shown only one signal in the test lysate show both signals. These kinases are the group of kinases in the cell lysate, which are inhibited by the particular inhibitor tested.

The activation of kinases in cells is a well-known technique that is widely used in tissue culture laboratories. Depletion of fetal calf serum or other sera will starve cells. After starvation adding fetal calf serum (FCS) or other sera induces the activation of kinases. The activation can also be induced by growth factors and cytokines as e.g. EGF, VEGF, PDGF, HGF, TGF, NGF, FGF, insulin, various interleukines, and interferon. The growth factors and cytokines have to be applied as a cocktail for the induction of multiple kinases. The activation results in autophosphorylation of different kinases.

The main embodiment is a method for detecting modification sites of a protein or polypeptide in an analyte of a sample to be analyzed comprising said protein or polypeptide, wherein the modification site is selected from the group consisting of phosphorylation autophosporylation, methylation, hydroxylation, glycosylation, ubiquination, acetylation prenylation, amidation or N-terminal methionine detection, the method comprising
  (a) providing a first capture antibody that is specific for or binds to said modification site and is conjugated or associated with a dye serving as detection marker, and
  (b) providing a second antibody that is specific for or binds to said protein on a site or epitope which is different from said modification site, and which is conjugated or associated with a detection marker which is distinguishable from said dye of step (a),
(c) providing a third capture antibody that is specific for or binds to another modification site as used in (a) and is conjugated or associated with a dye serving as detection marker which is distinguishable from said dye of step (a) and (b).

Another preferred embodiment is a method of wherein the modifications analyzed by the invention are but not limited to phosphorylation, autophosphorylation, methylation, hydroxylation, glycosylation, ubiquination, acetylation, prenylation, amidation or N-terminal Methionine detection regarding MetAP1 and MetAP2 enzyme activity confirmation. The modifications analyzed by the invention are but not limited to phosphorylation, methylation hydroxylation, glycosylation, ubiquination, acetylation, prenylation or amidation.

Another preferred embodiment of the invention is a method for analysing the autophosphorylation of one or more kinases with the method above in presence of a kinase inhibitor compared to the absence of said kinase inhibitor, the method comprising the steps:
(a) starving cells by serum depletion,
(b) inducing of kinase autophosphorylation activity by adding serum, growth factors and/or cytokines in presence and in absence of a kinase inhibitor,
(c) solubilizing the cells thereby releasing cell lysate there from,
(d) capturing the kinases in the cell lysate by adding different phospho tyrosine, phospho serine, phospho threonine and non-modification site specific binding protein conjugated with different dyes,
wherein each different binding protein is associated with an unique dye,
(e) identifying the autophosphorylated tyrosine kinases that have unique dyes from d) by an antibody which bind to a non-modification site specific region on the kinase which is directly conjugated to the read out label or coupled to Biotin, wherein the antibody must bind to another non-modification site specific region in the kinase as the binding protein used for d).
(f) comparing the autophosphorylated tyrosine kinases from e) resulting from an induction in presence of a kinase inhibitor with the induction in absence of said kinase inhibitor and comparing the autophosphorylated kinase from e) in direct comparison with the non modified kinase level in each individual cavity, which allows the normalization of each individual analyte.

Another preferred embodiment is method described above wherein the analyzed modifications detect MetAP1 and MetAP2 enzyme activity confirmation.

The used dyes are preferable but not limited fluorescence or luminescence dyes.

Another part of the invention is a method wherein under step b) is tested a kinase activator instead of a kinase inhibitor.

A further embodiment of the invention is a method for measuring the phosphorylation of one or more protein kinases downstream of receptor tyrosine kinases. These phosphorylation is an autophasphorylation or a phosporylation of an upstream kinase. The kinases can be but not limited to serine kinases, threonine kinases or histidin kinases.

A further embodiment of the invention is a method for measuring the phosphorylation and/or autophosphorylation of one or more protein kinases downstream of receptor tyrosine kinases in presence of a kinase inhibitor compared to the absence of said kinase inhibitor, the method comprising the steps:
(a) starving cells by serum depletion,
(b) inducing of kinase autophosphorylation activity by adding serum, growth factors and/or cytokines in presence and in absence of a kinase inhibitor,
(c) solubilizing the cells thereby releasing cell lysate there from,
(d) capturing the kinases in the cell lysate by adding different phospho tyrosine, phospho serine, phospho threonine and non-modification site specific binding protein conjugated with different microspheres,
wherein each different binding protein is associated with an unique dye,
(e) identifying the autophosphorylated tyrosine kinases that have unique dyes from d) by an antibody which bind to a non-modification site specific region on the kinase which is directly conjugated to the read out label or coupled to Biotin, wherein the antibody must bind to another non-modification site specific region in the kinase as the binding protein used for d).
(f) comparing the autophosphorylated tyrosine kinases from e) resulting from an induction in presence of a kinase inhibitor with the induction in absence of said kinase inhibitor and comparing the autophosphorylated kinase from e) in direct comparison with the non modified kinase level in each individual cavity, which allows the normalization of each individual analyte.

The dyes and marker are luminescence and/or fluorescence dyes or markers, respectively.

Method mentioned above for profiling the phosphorylation status of tyrosine kinases, in absence of a kinase inhibitor,
wherein the lysates of claim 1 c) are derived from tumor specimen, a disease affected tissue or comparable animal material,
for diagnosis and tumor staging.

In another embodiment of the invention is a transformation prior to cell starvation, with a nucleic acid encoding a polypeptide of a protein that is able to induce phosphorylation or it the kinase itself in the cells.

The cells can be eukaryotic cells and in a preferred embodiment the cells are mammalian cells.

Another preferred embodiment is the use of the method above for profiling kinase inhibitors and kinase activators for their specificity to bind particular kinases.

Another preferred embodiment is a kit for the methods mentioned above for profiling the specificity of kinase inhibitors comprising:
(a) a composition of microspheres with 1-500 unique dyes associated with a different capture anti phospho-antibodies which binds phosphorylated kinases and,
(b) an antibody specific for a kinase labeled with a dye distinguishable from the dyes in a) for the identification of the phosphorylated kinase.

Another part of the invention is a kit mentioned above for profiling a kinase activator instead of a kinase inhibitor.

Another part of the invention is a kit for use in a method mentioned above for profiling the specificity of kinase inhibitors comprising:
(a) a composition of 1-500 unique dyes associated with different anti phospho antibodies
(b) an anti kinase antibody labeled with a dye distinguishable from the dyes in a).

Another part of the invention is a kit for use in a method mentioned above for profiling the specificity of kinase activators comprising:
(a) a composition of 1-500 unique dyes associated with different anti phosphor antibodies
(b) an anti kinase antibody labeled with a dye distinguishable from the dyes in a).

The dyes and marker used in the kit are luminescence and/or fluorescence dyes or markers, respectively.

Another aspect of the invention is a composition containing 1-500 unique dyes each associated with one different capture antibody which binds specifically to a definite modification or non-modification site in a kinase which has an epitope to which the capture antibody can specifically bind, for the measurement of autophosphorylation from 1-500 different kinases in combination with different phosphorylation sites in parallel.

The number of unique dyes can be between 1 and 500 for the measurement of autophosphorylation from 1-500 different kinases in combination with different phosphorylation sites in parallel.

A preferred number of individual kinases that can be measured in parallel are between 1-20, 1-40, 1-60 and 1-80 kinases and so on. Alternatively three different sites in kinase A, five different sites in kinase B, six different sites in kinase C could combined with an further number of X different sites in kinase Y, whereas the target site in the kinases could be non-modified or modified at different positions in the protein.

Another embodiment of the invention are compositions mentioned above with 1-100 or 1-200 or 1-300 or 1-400 unique fluorescent dyes colored microspheres.

The method, the kit and the composition can be used for the specificity profiling of each potential kinase inhibitor by measurement of autophosphorylation from 1-500 different kinases in parallel in presence of the kinase inhibitor in comparison to measurement of autophosphorylation from 1-500 different kinases in parallel in absence of the kinase inhibitor. A Luminex™ instrument can be used for the measurement of autophosphorylation. The kinase inhibitor can inhibit kinases that show autophosphorylation only in absence of the kinase inhibitor.

The method can be performed in a microtiter plate.

Another use for the method of the invention is the profiling of the auto phosphorylation status of various kinases in tumor specimen. The status of activity from various kinases gives a reflective hint for the diagnosis and the suitable therapeutic strategy to cure the patient (Espina V. et al. (2005) Cancer Invest, 23(1), pp. 36-46). In this particular case the sample that has to be analyzed would be a lysate from a tumor specimen or a disease affected tissue (biopsies or laser capture micro dissection) or also comparable animal material. The analysis can be done as described above in absence of a kinase inhibitor.

EXAMPLES

Example 1: Description of the Cellular Assay

Tumor cell lines were plated in 24 well plates at a density of 100000 to 200000 cells per well and cultivated in growth medium for 24 hours. After that period the cells were washed twice with starvation medium containing 0.05% BSA to remove all growth factors present in the growth medium. The cells were cultivated another 20 hours overnight in the presence of starvation medium (generally basal medium without any additives) to reduce the phosphorylation status of the target analytes of interest. For inhibitor incubation the starvation medium is changed to starvation medium containing the inhibitor with the indicated concentrations and incubated for 1 hour at 24° C. in a cell culture incubator. To induce the phosphorylation of the target analyte of interest the cells were stimulated with an optimal concentration of a growth factor or cytokine which able to induce its activation in the presence of the pre-incubated inhibitor. The necessary stimulation time is specific for each pathway and must be pre-evaluated. After the stimulation the incubation medium is completely removed and the cells are lysed in lysis buffer containing different protease and phosphatase inhibitors at 4° C. The cell lysates were harvested and stored until final analysis at −80° C. in small aliquots. For the calculation of the maximal stimulation/phosphorylation of the cells, controls were included on each individual 24 well plate which were not incubated with inhibitor and left untreated or stimulated with the stimulus only.

For the analysis of c-Met different cell lines were stimulated with recombinant human HGF to induce c-Met phosphorylation. The cells were treated before stimulation with increasing concentrations of inhibitors for 1 hour. Control cells are treated with the solvent only and used to calculate the % of control (HGF stimulated). To demonstrate the reduced basal level of phosphorylation after the starvation period cells treated with the solvent are additionally not stimulated with HGF (no inhibitor/no HGF). Such a control is absolutely necessary if autocrine cell lines are analysed in this setting because these cells are able to produce HGF which could induce a significant phosphorylation level before inhibitor incubation.

Example 2: Description Inverse c-Met Luminex Multiplex Assay

The described inverse assay format for c-Met kinase uses 3 or 4 different capture antibodies coupled to three or four different fluorescent dye colored microspheres. One of these antibodies is directed against the extracellular domain (ECD) of the receptor tyrosine kinase c-Met whereas the other antibodies bind different phosphorylation sites in the intracellular kinase domain (e.g. $Y^{1234}Y^{1235}$, $Y^{1349}$ and $Y^{1003}$). Alternatively an antibody directed against the intracellular domain (ICD) of c-Met could also be used for the detection of the total c-Met amount, if this antibody does not interfere with the antibodies which detect the phosphorylation sites in the ICD. This approach allows the parallel measurement of the total amount of c-Met in the identical sample with its activation status due the detection of the different phosphorylation sites. For capturing the sample is incubated with the mixture of the different antibody coupled microspheres for 20 hours at 4° C. under continuous agitation on a microplate shaker in serial dilution which allows the simultaneous measurement of high and low analyte concentrations (if the dynamic range of the measurement is not sufficient). After three washing cycles with a microplate washer the analyte captured microspheres are incubated with the detection antibody for one hour at 22° C. under continuous agitation on a microplate shaker. This detection antibody is directed to the ECD of c-Met but binds to a different epitope as the used capture antibody for total c-Met. Therefore competition effects between these two antibodies are avoided. Alternatively a polyclonal antibody against the ECD of c-Met could be used because it binds to different epitopes and is not influenced through the already bound capture ECD specific antibody. Finally the used detection antibody must be conjugated to Biotin because anti species antibody conjugates are no useful alternatives because of the possible cross-reactivity's against the capture antibodies from different species. After the incubation with the detection antibody the microspheres are washed again three times as previously described and incubated with a Streptavidin-Phycoerythrin Conjugate. Streptavidin binds with high affinity to Biotin and label all microspheres with bound detection antibody with the reporter dye Phycoerythrin. After two more washing steps acquisition buffer is added to the microspheres for measurement. The amount of bound Phycoerythrin is equivalent to the amount of bound detection antibody and analyte on the individual microspheres and can be measured in the Luminex Analyzer. During the measurement each individual microsphere shows an individual Phycoerythrin reporter signal dependent of the amount of bound analyte and can be distinguished from the other fluorescent dye colored microsphere due to its individual classification signal.

For an exact quantification of the measured c-Met level in the sample a recombinant c-Met standard protein is used to determine the total c-Met concentration. This standard protein is measured in a dilution series side by side with the samples (on each individual plate) and defines the whole dynamic range of the assay. Based on measured concentration of c-Met in the sample dilutions the values of the different phosphorylation sites can be normalized to MFI (median fluorescence intensity=read out of the Luminex instruments) per ng c-Met.

The described assay was developed on the basis of a 96-well plate format which uses 50 or 25 µL sample volume. After the assay transfer to the 384-well plate format for measurement on the FlexMAP 3D Luminex Analyzer the sample volume could be further reduced to 10-12 µL in total which allows the measurement of the limited human biopsy sample material for the first time. Additionally all other reagents as capture microspheres, detection antibody and conjugate are also be saved due to this downscaling.

DESCRIPTION OF THE FIGURES

FIG. 1: Comparison of assay setups with c-Met kinase inhibitors

U87-MG glioma cells were stimulated in vitro with recombinant human HGF to induce c-Met phosphorylation. The cells were treated before stimulation with increasing concentrations of two c-Met kinase inhibitors (black circle/black triangle) for 1 hour. Control cells are treated with the solvent only and used to calculate the % of control (black square). The cell lysates were analyzed with identical dilutions in two different assay setups. The standard single plex setup (upper graph) uses a c-Met capture antibody with phospho c-Met detection antibodies whereas the inverse assay setup is a 4-plex assay (lower graph) containing three different phospho c-Met capture antibodies directed to the phosphorylation sites $Y^{1234}Y^{1235}$, $Y^{1349}$ and $Y^{1003}$ and a total protein c-Met capture antibody specific for the extracellular domain of the receptor and another different ECD specific c-Met antibody for detection. While the two different phospho c-Met antibodies in the standard assay setup must be measured with two different assays side by side (one analyte=one cavity) the same phospho c-Met antibodies were measured in one assay as a 4-plex format with the inverse assay setup (four analytes=one cavity). Highly comparable $IC_{50}$ values for both c-Met kinase inhibitors were found with both assays setups for the two c-Met phosphorylation sites c-Met $Y^{1234}Y^{1235}$ (FIG. 1a) and c-Met $Y^{1349}$ (FIG. 1b) whereas the detection of the phosphorylation site $Y^{1003}$ was impossible because of the low c-Met expression level of U87-MG. The in parallel measured c-Met total protein show no influence at all concentrations of the c-Met kinase inhibitors. In addition these c-Met values could be used to normalize the measured phospho c-Met values.

Figure 1A:
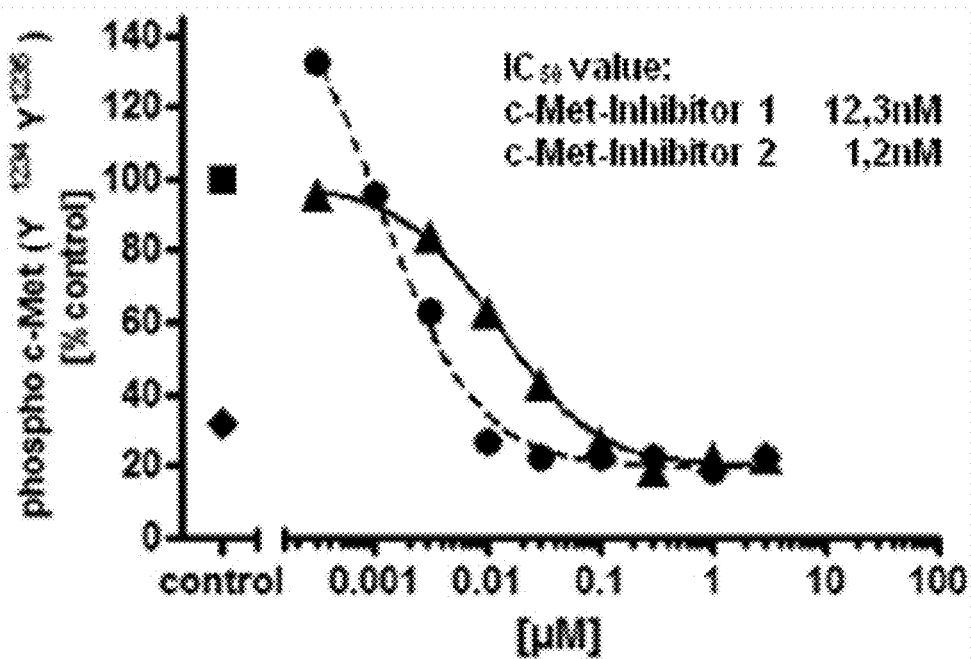
FIG. 1a is a graph
Figure 1A:
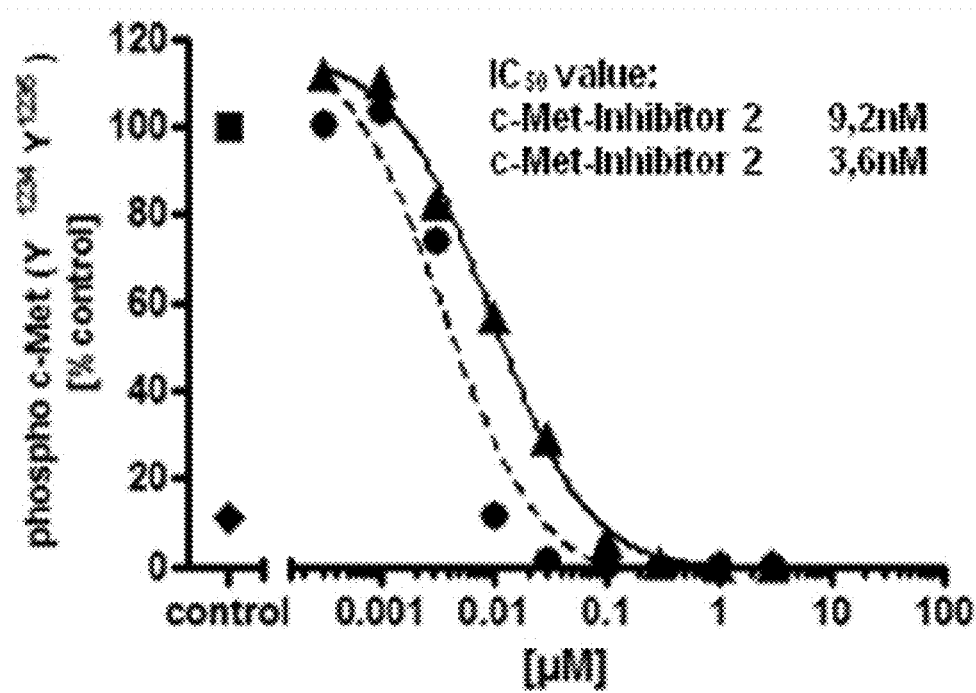
Figure 1B:
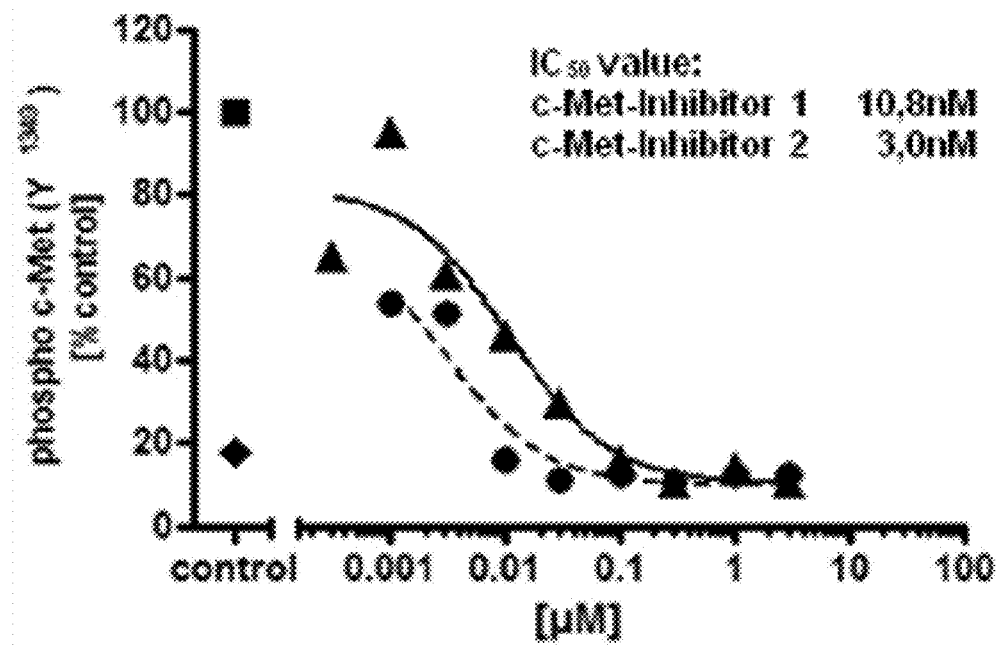
FIG. 1b is a graph
Figure 1B:
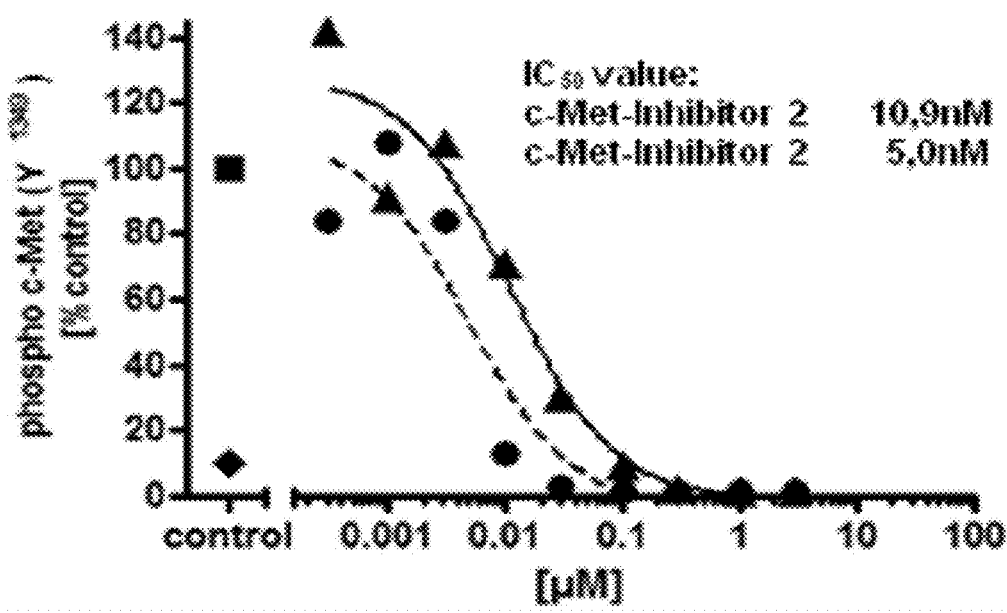
Figure 2A:
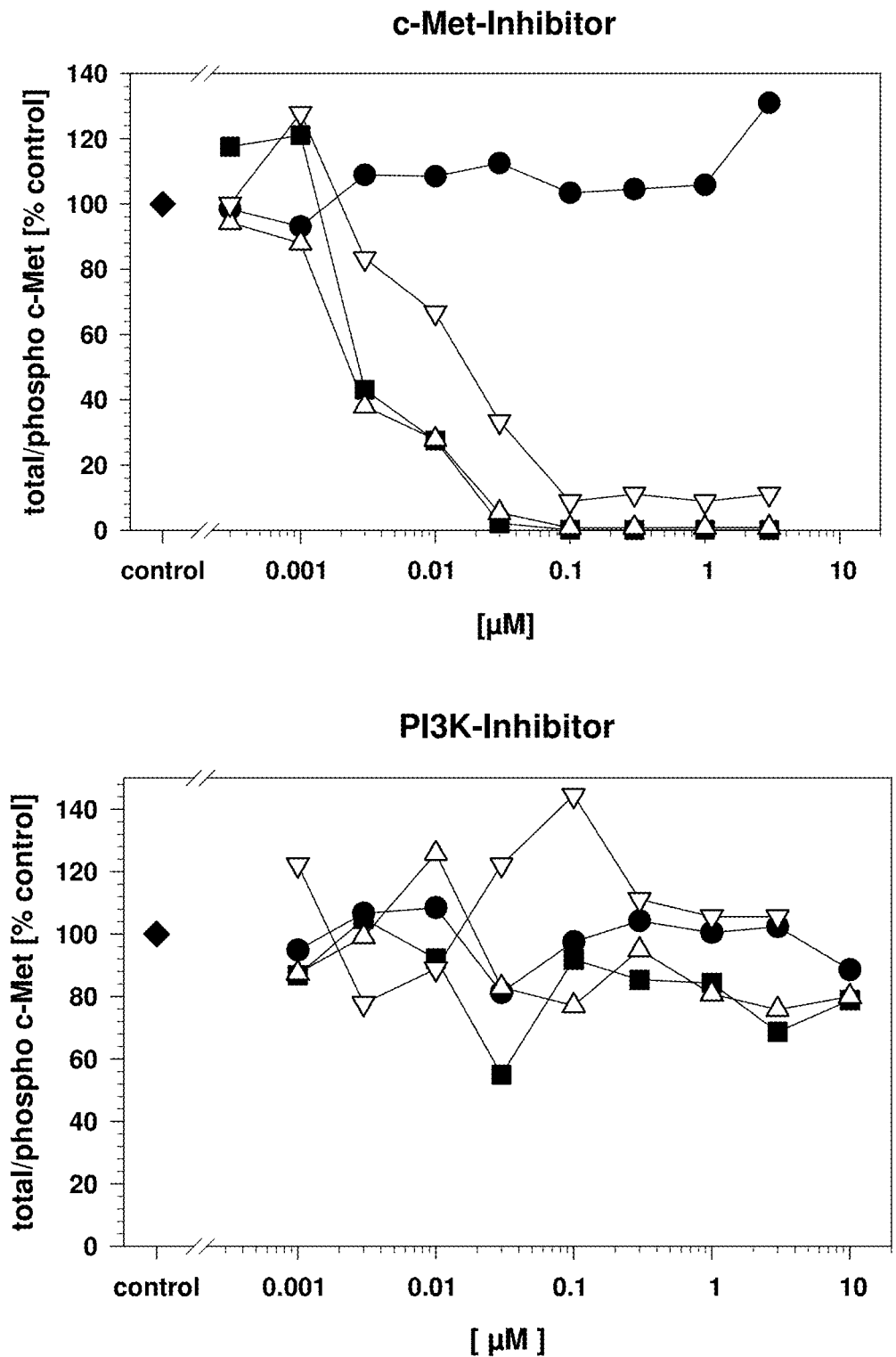
FIG. 2a is a graph
Figure 2B:
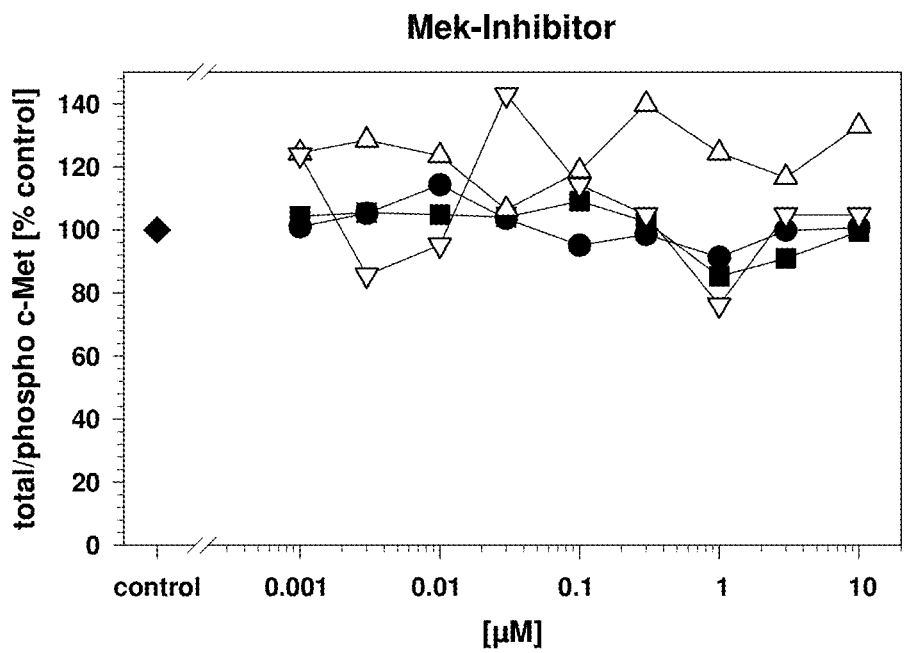
FIG. 2b is a graph
Figure 2B:
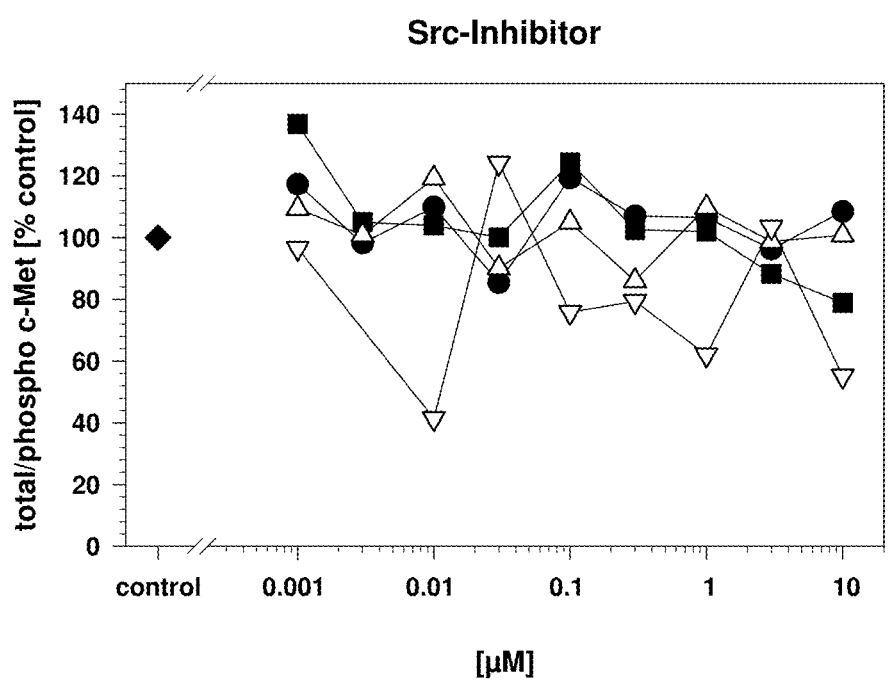
Figure 3A:
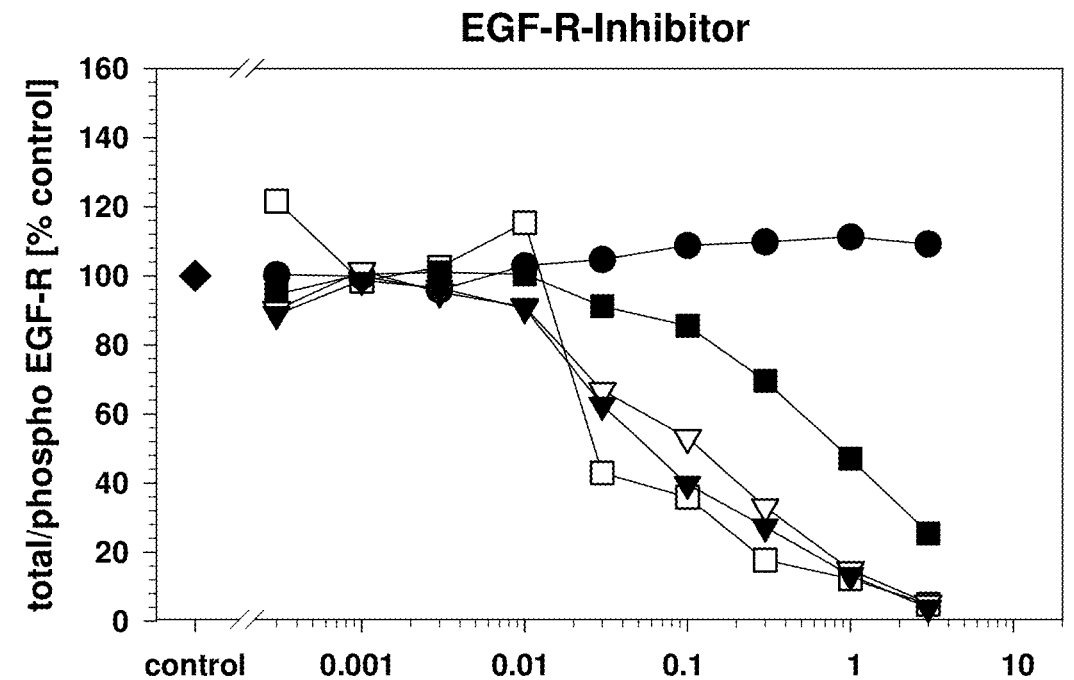
FIG. 3a is a graph
Figure 3A:
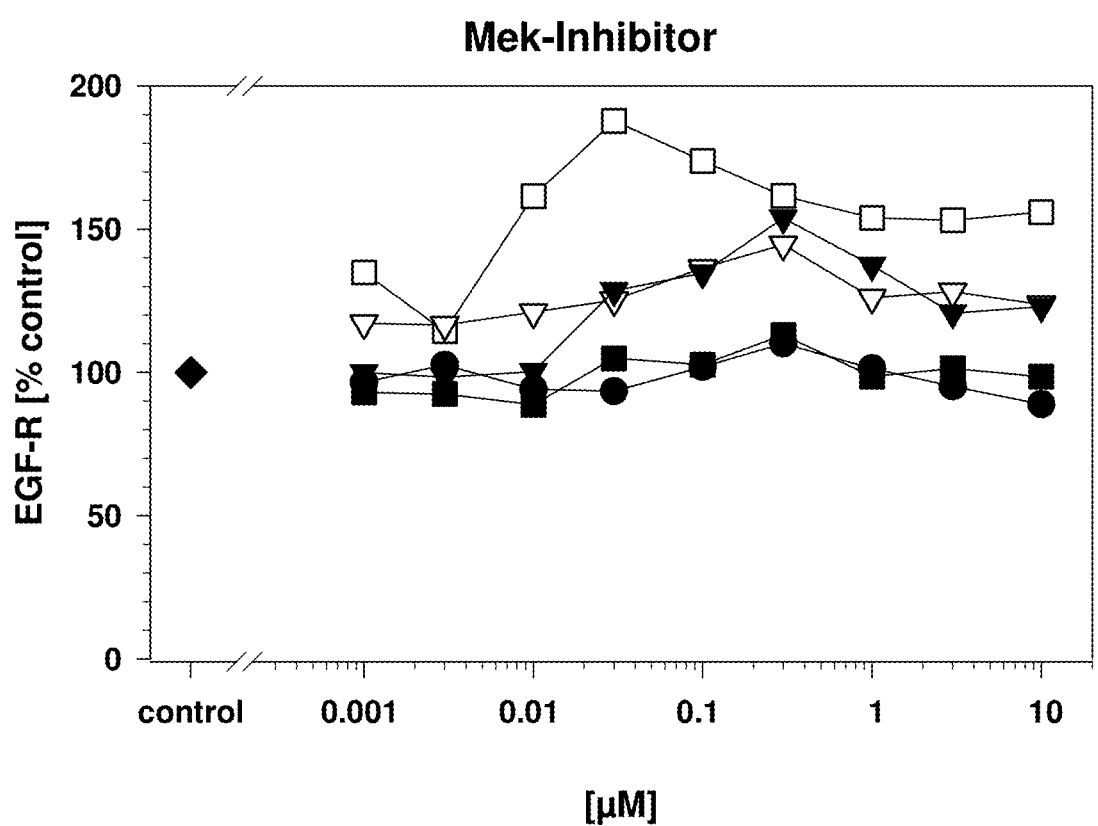
Figure 3B:
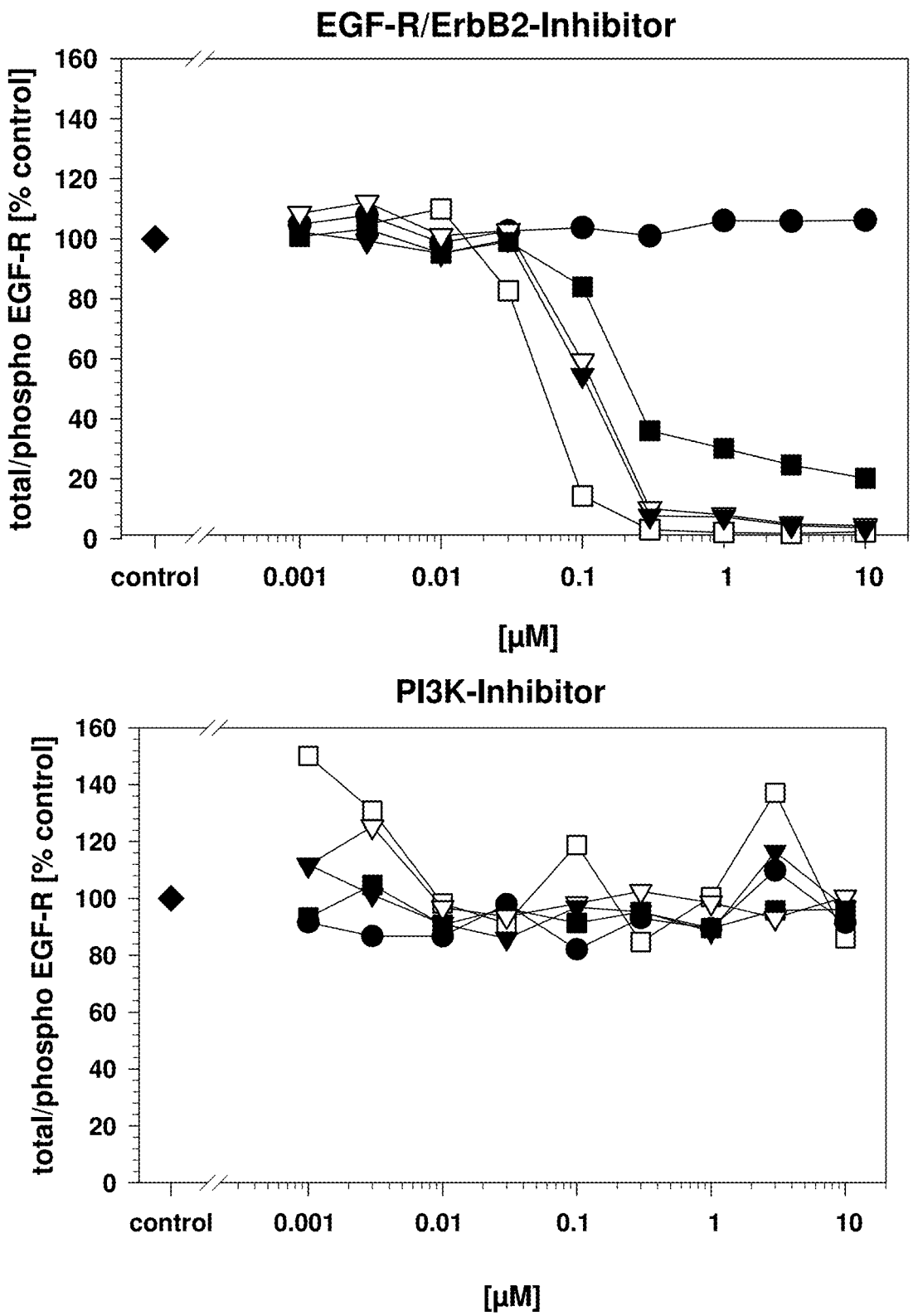
FIG. 3b is a graph
Figure 3C:
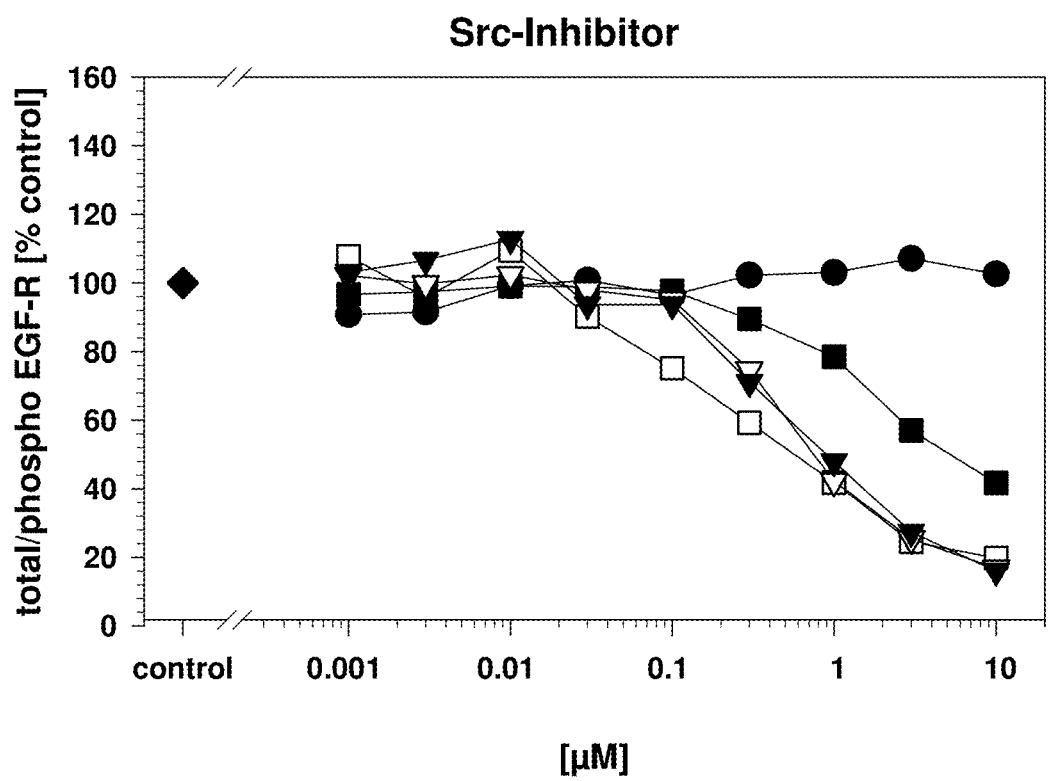
FIG. 3c is a graph

FIG. 2: Specificity of c-Met phospho protein detection after inhibition with different pathway kinase inhibitors A431 carcinoma cells were stimulated in vitro with recombinant human HGF to induce c-Met phosphorylation as described in FIG. 1 and incubated with different specific kinase inhibitors as described in FIG. 1. The cell lysates were analyzed in a c-Met 4-plex assay including total c-Met (black circle), phospho c-Met $Y^{1234}Y^{1235}$ (black square), phospho c-Met $Y^{1349}$ (white triangle up) and phospho c-Met $Y^{1003}$ (white triangle down) to evaluate the influence of the pathway specific inhibitors. Only the c-Met kinase inhibitor shows a dose dependent inhibition of all c-Met phosphorylation sites $Y^{1234}Y^{1235}$, $Y^{1349}$ and $Y^{1003}$ (FIG. 2a upper graph) whereas the inhibitors for PI3K (Phosphoinositide 3-kinase; FIG. 2a lower graph) and Mek (MAPK kinase or Erk kinase; FIG. 2b upper graph), Src (cellular und sarcoma kinase; FIG. 2b lower graph) have no effect on c-Met phosphorylation.

FIG. 3: Specificity of EGF-R phospho protein detection after inhibition with different pathway kinase inhibitor A431 carcinoma cells were stimulated in vitro as described in FIG. 1 with recombinant human EGF to induce EGF-R phosphorylation and incubated with different kinase inhibitors as described in FIG. 1. The cell lysates were analyzed in an EGF-R 5-plex assay including total EGF-R (black circle), and the EGF-R phosphorylation sites $Y^{845}$ (black triangle down), $Y^{998}$ (black square), $Y^{1086}$ (white square) and $Y^{1173}$ (white triangle down) to evaluate the influence of the pathway specific inhibitors. The EGF-R (FIG. 3a upper graph) and the dual EGF-R/ErbB2 inhibitor (FIG. 3b upper graph) shows a dose dependent inhibition of all EGF-R phosphorylation sites $Y^{845}$, $Y^{998}$, $Y^{1086}$ and $Y^{1173}$ whereas the inhibitors for Mek (MAPK or Erk kinase; FIG. 3a lower graph) and PI3K (Phosphoinositide 3-kinase; FIG. 3b lower graph) have no effect. The Src (cellular und sarcoma kinase; FIG. 3c) inhibitor has also an inhibition effect on the EGF-R phosphorylation in a clearly higher concentration range as the target specific inhibitors and is well explainable with the lateral signaling between the EGF-R and Src (Dulak et al.: 2011; Oncogene. 2011 Aug. 18; 30(33): 3625-3635). All inhibitors used show no influence on the measurement of total EGF-R in the 5-plex assay and the total EGF-R levels could be used for an exact normalization of the phosphorylation site values.

Figure 4:
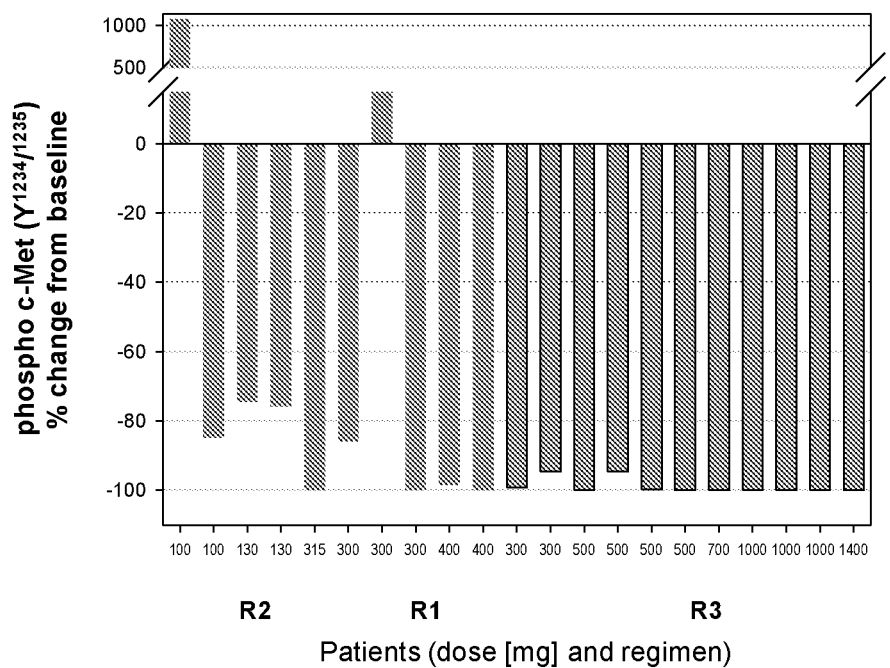
FIG. 4 is a graph

FIG. 4: Phospho-c-Met inhibition in tumor biopsies

Phospho c-Met levels were measured quantitatively in patient pre- and on-treatment tumor biopsy samples using an inverse 3-plex c-Met assay in a 384 well format. Miniaturization allows the measurement of three different target specific assays in one sample with biopsy material smaller than 0.5 mg. The two c-Met phosphorylation sites $Y^{1234}Y^{1235}$ and $Y^{1349}$ were analyzed and quantitatively normalized with the total c-Met concentrations measured in the identical sample. Results of the autophosphorylation site $Y^{1234}Y^{1235}$ are shown whereas the downstream signaling site $Y^{1349}$ shows comparable results with a slightly lower target inhibition. This target inhibition was observed in 19/21 evaluable patients. With doses 300 mg in R3 (once daily continuous dosing) ≥90% phospho-c-Met inhibition was observed in all biopsy-evaluable patients.

The invention claimed is:

1. A method for detecting modification sites of a protein or polypeptide in an analyte of a sample to be analyzed comprising said protein or polypeptide, wherein the modification site is selected from the group consisting of phosphorylation, autophosphorylation, methylation, hydroxylation, glycosylation, ubiquination, acetylation, prenylation, amidation or N-terminal methionine modification sites, comprising
    (a) contacting the sample with a first capture antibody that is specific for or binds to a first modification site and is conjugated or associated with a dye serving as a first detection marker,
    (b) contacting the sample with a second antibody that is specific for or binds to said protein or polypeptide at a protein- or polypeptide-specific site or epitope, which protein- or polypeptide-specific antibody binding site or epitope is different from the modification site in (a), and which second antibody is conjugated to or associated with a second detection marker which is distinguishable from said dye of step (a),
    (c) contacting the sample with a third capture antibody that is specific for or binds to a second modification site on said protein or polypeptide that is different from the first modification site in (a) and which second modification site is different from the protein- or polypeptide-specific site or epitope, and which third capture antibody is conjugated or associated with a dye serving as a third detection marker which is distinguishable from the detection markers of step (a) and step (b),
    (d) separating unbound protein or polypeptide from said antibodies, and
    (e) detecting the presence of bound detection markers.

2. A method for analyzing the phosphorylation and autophosphorylation of one or more kinases detected by the method of claim 1, in presence of a kinase inhibitor compared to the absence of said kinase inhibitor, comprising the steps:
    (a) starving cells by serum depletion,
    (b) inducing kinase auto phosphorylation activity by adding serum, growth factors and/or cytokines in presence and in absence of a kinase inhibitor,
    (c) solubilizing the cells thereby releasing cell lysate therefrom,
    (d) capturing the kinases in the sample by adding different phospho tyrosine, phospho serine, phospho threonine and non-modification site specific binding protein conjugated with different dyes,
        wherein each different binding protein is associated with an unique dye,
    (e) identifying the autophosphorylated tyrosine kinases that have unique dyes from (d) by an antibody which bind to a non-modification site specific region on the kinase which is directly conjugated to the read out label or coupled to Biotin, wherein the antibody must bind to another non-modification site specific region in the kinase as the binding protein used for (d),
    (f) comparing the phosphorylated or autophosphorylated tyrosine kinases from (e) resulting from an induction in presence of a kinase inhibitor with the induction in absence of said kinase inhibitor inhibitor and comparing the phosphorylated/autophosphorylated kinase from (e) in direct comparison with the non modified kinase level in each individual cavity, which allows the normalization of each individual analyte.

3. The method of claim 2, wherein the analyzed modifications detects MetAP1 and MetAP2 enzyme activity confirmation.

4. The method of claim 2, for profiling the phosphorylation status of tyrosine kinases, in absence of a kinase inhibitor,
    wherein the lysates of (c) are derived from tumor specimen, a disease affected tissue or comparable animal material, and
    wherein the phosphorylation status is correlated to diagnosis and tumor staging.

5. The method of claim 3, wherein in step (b), a kinase activator is tested.

6. The method of claim 1, wherein the dyes are selected from a fluorescence or luminescence dye.

7. The method of claim 1, wherein the markers are selected from a fluorescence or luminescence marker.

8. The method of claim 2, wherein the cells are transformed prior to cell starvation (a), with a nucleic acid encoding a polypeptide that represent the analyte of interest which is able to induce phosphorylation due to overexpression or because of an auto activating mutation in the recombinant peptide of kinase itself in said cells.

9. The method of claim 2, wherein the cells are eukaryotic cells.

10. The method of claim 2, wherein the eukaryotic cells are mammalian cells.

11. The method of claim 2, which additionally comprises profiling a kinase inhibitor for its specificity to bind a kinase, by determining which phosphorylation modification site or sites on the protein or polypeptide that is the target of the kinase are bound by the first and/or second capture antibody specific for the phosphorylation site or sites.

12. The method of claim 2, which additionally comprises profiling a kinase activator for its specificity to bind a kinase, by determining which phosphorylation modification site or sites on the protein or polypeptide that is the target of the kinase are bound by the first and/or second capture antibody specific for the phosphorylation site or sites.

13. The method of claim 1, wherein the protein or polypeptide is a kinase having phosphorylation modification sites, and/or wherein the sample further comprises a protein or polypeptide that is a target of the kinase and having a phosphorylation site, and which additionally comprises profiling a kinase inhibitor for its specificity to bind a kinase, by determining which phosphorylation modification site or sites on the protein or polypeptide that is the target of the kinase are bound by the first and/or third capture antibody specific for the phosphorylation site or sites.

14. The method of claim 1, wherein the protein or polypeptide is a kinase having phosphorylation modification sites, and/or wherein the sample further comprises a protein or polypeptide that is a target of the kinase and having a phosphorylation site, and which additionally comprises profiling a kinase activator for its specificity to bind a kinase, by determining which phosphorylation modification site or sites on the protein or polypeptide that is the target of the kinase are bound by the first and/or third capture antibody specific for the phosphorylation site or sites.

* * * * *